United States Patent

Halloran et al.

[11] Patent Number: 5,910,302
[45] Date of Patent: Jun. 8, 1999

[54] HAIR CONDITIONING WITH BLENDED SILICONES

[75] Inventors: Daniel Joseph Halloran, Midland; Kenneth A. Kasprzak, Saginaw, both of Mich.; Patricia D. Herter, Foster City, Calif.

[73] Assignee: Dow Corning Corporation, Midland, Mich.

[21] Appl. No.: 08/254,852

[22] Filed: Jun. 6, 1994

Related U.S. Application Data

[62] Division of application No. 07/972,342, Nov. 6, 1992.

[51] Int. Cl.$^6$ ................. A61K 7/07; A61K 7/00
[52] U.S. Cl. ..................... 424/70.122; 424/70.12
[58] Field of Search ............ 424/70.12, 70.122, 424/70.11, 70.1

[56] References Cited

U.S. PATENT DOCUMENTS

| | | | |
|---|---|---|---|
| 4,122,029 | 10/1978 | Gee | 252/309 |
| 4,265,878 | 5/1981 | Keil | 424/68 |
| 4,421,769 | 12/1983 | Dixon | 424/358 |
| 5,100,657 | 3/1992 | Ansher-Jackson | 424/70.12 |
| 5,104,646 | 4/1992 | Bovich | 424/70.12 |

*Primary Examiner*—Sally Gardner-Lane
*Attorney, Agent, or Firm*—James De Cesare

[57] ABSTRACT

A cosmetic composition for use in the treatment of hair. The cosmetic composition contains a conditioning agent and the improvement resides in the conditioning agent being a mixture of (i) a silicone polyether and (ii) an amine functional siloxane polymer. The amine functional siloxane polymer has the formula:

$$R_{3-z}'Q_zSiO[R_2'SiO]_d[R'QSiO]_bSiQ_zR_{3-z}'.$$

A method of treating hair is also described in which the mixture is applied to hair for the purpose of improving wet and dry combing and imparting durable conditioning benefits to the hair.

5 Claims, No Drawings

HAIR CONDITIONING WITH BLENDED SILICONES

This is a divisional of copending application Ser. No. 07/972,342 filed on Nov. 6, 1992.

BACKGROUND OF THE INVENTION

This invention is directed to the conditioning of hair with a composition which includes the combination of a silicone polyether and an amine functional polysiloxane fluid. Such blends have been found to impart improved conditioning benefits to the hair.

Hair preparations are compositions which are employed on the scalp or hair. The most important hair preparations are shampoos, conditioning products, colorants, hairstyling preparations including setting lotions and hairsprays, and permanent wave preparations.

Shampoos are mild cosmetic products for cleaning the hair and scalp. Hair becomes soiled due to skin flakes, sebum, perspiration, dust, and residues from sprays, lotions and conditioning agents. Shampoos are-designed to leave the hair clean, pliable, lustrous, possessing a pleasant odor, and easy to untangle, comb, manage, and style. The principal ingredient of a shampoo is a surfactant which functions to release dirt from the hair and to transport it to the aqueous medium. Since consumers equate lathering with cleanliness, anionic surfactants such as alkyl sulfates and sulfonates are preferred because of their high lather. Numerous other constituents are included in shampoos such as thickeners to prevent the shampoo from running down the face into the eyes, opacifiers to provide a rich pleasing pearlescent appearance, buffers to adjust the pH of the shampoo to a value which is gentle to the skin, and fragrances to impart a pleasant aroma to the washed hair following rinsing. Most frequently, shampoos are marketed as clear products although gels having a higher viscosity and packaged in tubes, and pearlescent compositions are available.

With the advent of consumer trends toward daily hair washing, conditioning shampoos have emerged which are designed to render the hair easy to comb and tangle free in the wet state, as well as glossy and soft when dry. Such conditioning is provided by the inclusion in the shampoo of an organic cationic polymer which upon rinsing produces a thin film on the hair. This film functions as a lubricant when the:hair is wet and prevents static charge and "flyaway" when the hair is dry.

Conditioning may also be provided by hair conditioning products designed solely for that purpose such as rinses, mousses, aerosols, and pump sprays, which conditioners are applied following shampooing. These conditioning products are rinsed from the hair a short time following their application. Such conditioners prevent excessive split ends and other mechanical hair damage and roughening, and seek to neutralize the adverse effects which hair undergoes due to humidity, temperature, exposure to sunlight, frequent washing, combing, and brushing, and cosmetic treatments such as bleaching, dyeing, and waving.

The present invention provides a viable alternative to hair conditioning with cationic organic polymers, and provides an organosilicon conditioning additive which not only achieves conditioning on the level obtained with organic conditioners, but which in addition results in an unexpected "synergy" obtained when certain silicone polymers are combined. Not only do the blended silicones provide improved wet combining, but they in addition impart durable and long lasting conditioning benefits, in comparison to single silicones traditionally noted for their conditioning effect.

SUMMARY OF THE INVENTION

The invention is directed to the treatment and conditioning of hair with a cosmetic composition which includes as a conditioning agent for the hair a mixture of a silicone polyether and an amine functional silicone. Such mixtures have been found to improve the wet combing characteristics of hair while at the same time providing durable and more efficacious conditioning effects.

The invention is also directed to a composition in the form of a mixture of the silicone polyether and the amine functional silicone, which mixture is of general application in the personal care field including treatment of the hair and skin. Aesthetically, the mixture will rub-out to a smooth soft feel. Such perception is of importance in the consumer oriented personal care market.

These and other features, objects, and advantages, of the herein defined present invention will become more apparent from a consideration of the following detailed description thereof.

DETAILED DESCRIPTION OF THE INVENTION

The amine functional siloxane polymer employed in the blends in accordance with the present invention has the formula:

$R_{3-z}'Q_zSiO[R_2'SiO]_x[R'QSiO]_ySiQ_zR_{3-z}'$ wherein R' denotes an alkyl group of 1 to 4 carbons or a phenyl group with the proviso that at least 50 percent of the total number of R' groups are methyl; Q denotes an amine functional substituent of the formula —R"Z wherein R" is a divalent alkylene radical of 3 to 6 carbon atoms and Z is a monovalent radical selected from the group consisting of —NR₂''', and —NR''' (CH₂)ₙNR₂'''; wherein R''' denotes hydrogen or an alkyl group of 1 to 4 carbons, and n is a positive integer having a value of from 2 to 6; z has a value of 0 or 1; x has an average value of 25 to 10,000; y has an average value of 0 to 100 when z is 1, y has an average value of 1 to 100 when z is 0; with the proviso that in all cases y has an average value that is not greater than one tenth the average value of x.

Suitable R' groups are represented by and may be independently selected from among methyl, ethyl, propyl, isopropyl, butyl, isobutyl, and phenyl, with the proviso that at least fifty percent of the R' groups are methyl.

The alkylene radicals represented by R" may include trimethylene, tetramethylene, pentamethylene, —CH₂CHCH₃CH₂—, and —CH₂CH₂CHCH₃CH₂—. Siloxanes where R" is a trimethylene or an alkyl substituted trimethylene radical such as —CH₂CHCH₃CH₂—, are preferred.

Alkyl groups of 1 to 4 carbon atoms as represented by R" include methyl, ethyl, propyl, isopropyl, butyl, and isobutyl.

Useful Z radicals include the unsubstituted amine radical —NH₂, alkyl substituted amine radicals such as —NHCH₃, —NHCH₂CH₂CH₂CH₃, and —N(CH₂CH₃)₂; and aminoalkyl substituted amine radicals such as —NHCH₂CH₂NH₂, —NH(CH₂)₆NH₂, and —NHCH₂CH₂CH₂N(CH₃)₂.

When z is zero, the silicone polymer has only pendent amine functional substituents in the polymer chain. When z is one, the silicone polymer may have only terminal amine functional substituents or both terminal and pendent amine functional substituents in the polymer chain. Preferably, x may vary from a value of 25 to 1000, and y may vary from zero to 100 when z is one and from one to 100 when z is zero. Most preferably, the value of x+y is in the range of about 50 to 1000.

The trisiloxane polyether of the present invention is a compound having the formula:

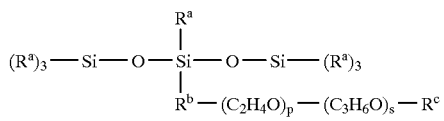

wherein $R^a$ is an alkyl group of one to six carbon atoms; $R^b$ is a linking group and a radical selected from the group consisting of —O—, —$C_mH_{2m}$—, —$C_mH_{2m}$O—, —$C_mH_{2m-2}$—, —$C_mH_{2m-2}$O—, and —$C_mH_{2m}CO_2$—; $R^c$ is a terminating radical which can be hydrogen, an acyl group, an aryl group, or an alkyl group of one to six carbon atoms; m has a value of two to eight; p and s have values such that the oxyalkylene segment —$(C_2H_4O)_p$—$(C_3H_6O)_s$— has a molecular weight in the range of 250 to 5,000; the segment having fifty to one hundred mole percent of oxyethylene units —$(C_2H_4O)_p$— and zero to fifty mole percent of oxypropylene units —$(C_3H_6O)_s$—.

Preferably, $R^a$ and the terminating radical $R^c$ are hydrogen, acetyl, or methyl groups; m is preferably three or four whereby the linking group $R^b$ is most preferably the radical —$(CH_2)_3$—O—; and the values of p and s are such as to provide a molecular weight of the oxyalkylene segment —$(C_2H_4O)_p$—$(C_3H_6O)_s$— of between 1,000 to 1,500. Methods of making such silicone polyether compounds are known in the art, and are described in detail for example, in the volume "Chemistry and Technology of Silicones", Walter Noll, Academic Press Inc., 1968, Pages 373–376.

The oxyalkylene segment —$(C_2H_4O)_p$—$(C_3H_6O)_s$— may consist of only oxyethylene units —$(C_2H_4O)_p$— or combinations of oxyethylene units —$(C_2H_4O)_p$— and oxypropylene units —$(C_3H_6O)_s$—.

The linking group $R^b$ between the silicon atom and the oxyalkylene segment may provide for a silicon-oxygen bond or a silicon-carbon bond, most preferably a silicon-carbon bond. In some instances it may be desirable to employ unsaturated linking groups such as the radical —$C_mH_{2m-2}$—, and the radical —$C_mH_{2m-2}$O—. Representative of such unsaturated linking group radicals $R^b$ are —CH=CH—C(CH$_3$)$_2$— and —CH=CH—C(CH$_3$)$_2$—O—.

The trisiloxane polyether of the present invention may in alternate embodiments take the form of an endblocked trisiloxane polyether in which the linking group $R^b$, the oxyalkylene segments, and the terminating radical $R^c$ occupy positions bonded to the ends of the trisiloxane chain. Such alternate forms may be represented by the following formula in which the various groups, radicals, segments, and integers, have the same meaning as defined above:

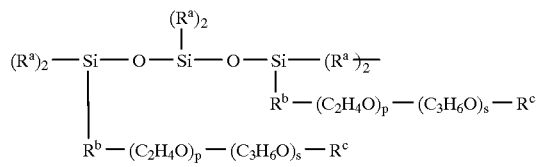

In some applications, it may be desirable to combine other organosilicon compounds with the amine functional silicone and the trisiloxane polyether, in which case a volatile silicone or a silicone gum would be appropriate.

The volatile silicone is appropriately a low viscosity methylsilicone fluid. The volatile low viscosity methylsilicone fluid corresponds to the average unit formula $(CH_3)_a SiO_{(4-a/2)}$ wherein a is an integer having an average value of from two to three. The methylsilicone fluid contains siloxane units joined by Si—O—Si bonds. Representative units are $(CH_3)_3SiO_{1/2}$, $(CH_3)_2SiO_{2/2}$, $(CH_3)SiO_{3/2}$, and $SiO_{4/2}$. These units are present in molar amounts such that there is an average of from about two to three methyl groups per silicon atom in the methylsilicone fluid, whereby the fluid has a viscosity of less than about one hundred centistokes measured at twenty-five degrees Centigrade.

The methylsilicone fluid contains dimethylsiloxane units and optionally trimethylsiloxane units. Preferably, the methylsilicone fluid has a viscosity of less than about ten centistokes, and can be either cyclopolysiloxane compounds of the general formula $[(CH_3)_2SiO]_x$ or linear siloxane compounds of the general formula $(CH_3)_3SiO[(CH_3)_2SiO]_y Si(CH_3)_3$. In both formulas, x is an integer having a value of from three to ten, and y is an integer having a value of from zero to about four.

Such volatile silicones have boiling points generally less than about two hundred-fifty degrees Centigrade, and viscosities preferably generally less than about ten centistokes measured at twenty-five degrees Centigrade. Most preferably the viscosity is between 0.65 to 5.0 centistokes. The cyclopolysiloxane compounds have been assigned the adopted name "CYCLOMETHICONE" by The Cosmetics, Toiletries and Fragrance Association, Inc., Washington, D.C. (CTFA). Both the cyclopolysiloxanes and the linear siloxanes are clear fluids, and are essentially odorless, nontoxic, nongreasy and nonstinging. Cosmetically, these volatile methylsilicone fluids are nonirritating to skin, and exhibit enhanced spreadability and ease of rub-out when applied. Once applied, the materials evaporate leaving behind no residue.

Methylsilicone fluids which are operable in accordance with the present invention leave substantially no residue after thirty minutes at room temperature when one gram of fluid is placed at the center of a No. 1 circular filter paper having a diameter of 185 mm supported at its perimeter in open room atmosphere. By methylsilicone fluid is meant a composition containing two or more silicon atoms, all of which are bonded by way of at least one oxygen atom to at least one other silicon atom and at least one methyl radical, each silicon valence not satisfied by oxygen being satisfied by a methyl radical.

Representative methylsilicone fluids found to be especially useful in the present invention are hexamethyldisiloxane which has a boiling point of 99.5 degrees Centigrade and the formula Me$_3$SiOSiMe$_3$; octamethyltrisiloxane which has a boiling point of 152 degrees Centigrade and the formula Me$_3$SiOMe$_2$SiOSiMe$_3$; hexamethylcyclotrisiloxane which has a boiling point of 133 degrees Centigrade and the formula [(Me$_2$)SiO]$_3$; octamethylcyclotetrasiloxane which has a boiling point of 171 degrees Centigrade and the formula [(Me$_2$)SiO]$_4$; and decamethylcyclopentasiloxane which has a boiling point of 205 degrees Centigrade and the formula [(Me$_2$)SiO]$_5$. These methylsilicone fluids may be used alone, or as mixtures in combinations of two or more of the individual fluids. Mixtures of the methylsilicone fluids will result in a volatile material having an evaporating behavior different from any one of the individual methylsilicone fluids. The methylsilicone fluids and their methods of preparation are known in the art, and such fluids are commercially available.

In some instances, it may be desirable to replace one or more of the methyl groups in the methylsilicone fluid with other groups. Thus, there may be substituted groups such as alkyl radicals having two to twelve carbon atoms; aryl radicals having six to ten carbon atoms; amine groups; vinyl; hydroxy; haloalkyl groups; aralkyl groups; and acrylate groups, for example.

The polydiorganosiloxane gum suitable for use in the present invention as an optional conditioning ingredient is a polydimethylsiloxane gum which can be represented by an average unit formula $$R_a SiO_{\frac{4-a}{2}}$$

where each R is a methyl radical, a vinyl radical, a phenyl radical, an ethyl radical or a 3,3,3-trifluoropropyl radical and a has an average value of 1.95 to 2.005 inclusive. Since the polydiorganosiloxane gums are essentially polydimethylsiloxane gums, at least 90 percent of the total R groups are methyl radicals and the remaining R groups are vinyl, phenyl, ethyl, of 3,3,3-trifluoropropyl. Small amounts of other groups can be present such as 1 or 2 percent of the total R, where such groups are other monovalent hydrocarbon groups, such as propyl, butyl, hexyl, cyclohexyl, beta-phenylethyl, octadecyl and the like; other halogenated monovalent hydrocarbon radicals, such as chloromethyl, bromophenyl, α,α, α-trifluorotolyl, perfluoroheptylethyl, dichlorophenyl and the like; cyanoalkyl; alkoxy, such as, methoxy, propoxy, ethoxy, hexoxy and the like; ketoxime; halogen; hydroxyl; aminoalkyl; and acyloxy. The groups which are present in small amounts are considered as incidental and not producing any significant characteristic changes of the polydimethylsiloxane gum.

The polydiorganosiloxane gums suitable for the present invention are essentially composed of dimethylsiloxane units with the other units being represented by monomethylsiloxane, trimethylsiloxane, methylvinylsiloxane, methylethylsiloxane, diethylsiloxane, methylphenylsiloxane, diphenylsiloxane, ethylphenylsiloxane, vinylethylsiloxane, phenylvinylsiloxane, 3,3,3-trifluoropropylmethylsiloxane, dimethylphenylsiloxane, methylphenylvinylsiloxane, dimethylethylsiloxane, 3,3,3-trifluoropropyldimethylsiloxane, mono-3,3,3-trifluoropropylsiloxane, aminoalkylsiloxane, monophenylsiloxane, monovinylsiloxane and the like.

The polydiorganosiloxane gums are well known in the art and can be obtained commercially, and are considered to be insoluble polydiorganosiloxanes which have viscosities greater than 1,000,000 cs. at 25° C., preferably greater than 5,000,000 cs. at 25° C.

These gums may be used alone as well as in admixture with one or more non-volatile or volatile ingredients such as a cyclic silicone. Volatile cyclic silicones which may be employed are polydimethylcyclosiloxanes exemplary of which are octamethylcyclotetrasiloxane and decamethylcyclopentasiloxane. The viscosity at 25° C. of the volatile cyclics is generally of the order of 2.5 to 6.0 cs. Such volatile ingredients are generally represented by the formula $(CH_3)_2SiO_x$ where x is 3–8. When used in admixture with the gum, the level of the cyclic is generally of the order of about thirteen percent by weight.

The compositions of this invention may contain a surfactant selected from the group consisting of anionic and amphoteric surfactants. The surfactant system should provide an acceptable level of foam on the hair and be capable of cleaning the hair, and may comprise one or more water soluble detergents, i.e., an anionic or amphoteric sur-factant. Suitable anionic detergents include sulfonated and sulfated alkyl, aralkyl and alkaryl anionic detergents; alkyl succinates; alkyl sulfosuccinates and N-alkyl sarcosinates. Especially preferred are the sodium, magnesium, ammonium, and the mono-, di- and triethanolamine salts of alkyl and aralkyl sulfates as well as the salts of alkaryl sulfonates. The alkyl groups of the detergents generally have a total of from about 12 to 21 carbon atoms, may be unsaturated, and are preferably fatty alkyl groups. The sulfates may be sulfate ethers containing one to ten ethylene oxide or propylene oxide units per molecule. Preferably, the sulfate ethers contain 2 to 3 ethylene oxide units.

Typical anionic-detergents include, among others, sodium lauryl sulfate, sodium lauryl ether sulfate, ammonium lauryl sulfate, triethanolamine lauryl sulfate, sodium C14–16 olefin sulfonate, ammonium pareth-25 sulfate (ammonium salt of a sulfated polyethylene glycol ether of a mixture of synthetic C12–15 fatty alcohols), sodium myristyl ether sulfate, ammonium lauryl ether sulfate, disodium monooleamidosulfosuccinate, ammonium lauryl sulfosuccinate, sodium dodecylbenzene sulfonate, triethanolamine dodecylbenzene sulfonate and sodium N-lauroyl sarcosinate. The most preferred anionic detergents are the lauryl sulfates, particularly monoethanolamine, triethanolamine, ammonium and sodium lauryl sulfates. Sodium lauryl ether sulfate is also very suitable for use in the compositions of this invention.

Surfactants generally classified as amphoteric or ampholytic detergents include, among others, cocoamphocarboxyglycinate, cocoamphocarboxypropionate, cocobetaine, N-cocamidopropyldimethylglycine, and N-lauryl-N-carboxymethyl-N-(2-hydroxyethyl)ethylenediamine. Other suitable amphoteric detergents include the quaternary cycloimidates, betaines, and sultaines disclosed in U.S. Pat. No. 3,964,500. The betaines may have the structure:

$$R^1R^2R^3N^+(CH_2)_mCOO^-$$

wherein $R^1$ is an alkyl group having about 12 to 18 carbon atoms or a mixture thereof, $R^2$ and $R^3$ are independently lower alkyl groups having 1 to 3 carbon atoms, and m is an integer from 1 to 4. Specific betaines useful in the products of the invention are for example alpha-(tetradecyldimethylammonio)acetate, beta-(hexadecyldiethylammonio)propionate, and gamma-(dodecyldimethylammonio)butyrate.

The sultaines may have the structure:

$$R^1R^2R^3N^+(CH_2)_mSO_3^-$$

wherein $R^1$, $R^2$, $R^3$, and m are defined as above. Specific useful sultaines are for example 3-(dodecyldimethylammonio)-propane-1-sulfonate, and 3-(tetradecyldimethylammonio)ethane-1-sulfonate.

The compositions of this invention may contain a nonionic surfactant. The nonionic surfactants of the present invention are selected from the group consisting of fatty acid alkanolamide and amine oxide surfactants. The fatty acid alkanolamides are nonionic surfactants obtained by reacting alkanolamines such as monoethanolamine, diethanolamine, monoisopropanolamine, or diisopropanolamine with a fatty acid or fatty acid ester to form the amide. The hydrophobic portion of the nonionic surfactant is provided by a fatty acid hydrocarbon chain which generally has from 10 to 21 carbon atoms. The fatty acid alkanolamide surfactants include, for example, fatty acid diethanolamides such as isostearic acid diethanolamide, lauric acid diethanolamide, capric acid diethanolamide, coconut fatty acid diethanolamide, linoleic acid diethanolamides, myristic acid diethanolamide, oleic acid diethanolamide, and stearic acid diethanolamide; fatty acid monoethanolamides such as coconut fatty acid monoethanolamide; and fatty acid monoisopropanolamides such as oleic acid monoisopropanoiamide and lauric acid monoisopropanolamide.

The amine oxides are well known nonionic surfactants usually obtained by oxidizing a tertiary amine to form the amine oxide. They are sometimes also referred to as polar nonionic surfactants. Amine oxide surfactants include, for example, the N-alkyl amine oxides such as N-cocodimethylamine oxide, N-lauryl dimethylamine oxide, N-myristyl dimethylamine oxide, and N-stearyl dimethylamine oxide; the N-acyl amine oxides such as N-cocamidopropyl dimethylamine oxide and N-tallowamidopropyl dimethylamine oxide; and N-alkoxyalkyl amine oxides such as bis(2-hydroxyethyl) $C_{12-15}$ alkoxy-propylamine oxide. The hydrophobic portion of the amine oxide surfactants is generally provided by a fatty hydrocarbon chain containing from 10 to 21 carbon atoms.

For purposes of this invention the alkanolamide and amine oxide surfactants are preferred. In general, the fatty acid diethanolamides and N-alkyl dimethylamine oxides are preferred for use in the compositions. Especially preferred are the fatty acid diethanolamides and N-alkyl dimethylamine oxides where the fatty hydrocarbon chain contains from 10 to 18 carbon atoms. For example, especially preferred nonionic surfactants include lauric acid diethanolamide, N-lauryl dimethylamine oxide, coconut acid diethanolamide, myristic acid diethanolamide, and oleic acid diethanolamide.

Additional categories of surfactant materials may also be included such as cationic and zwitterionic surfactants, and representative compounds are set forth in detail in U.S. Pat. No. 4,902,499, issued Feb. 20, 1990, which is considered to be incorporated herein by reference.

Other adjuvants may be added to the compositions of this invention such as thickeners, perfumes, colorants, electrolytes, pH control ingredients, foam boosters and foam stabilizers, antimicrobials, antioxidants, ultraviolet light absorbers and medicaments. For example, it is sometimes preferred to employ a thickener in the compositions to facilitate the hand application of the composition to the hair. Thickeners are preferably used in sufficient quantities to provide a more luxurious effect. For example, viscosities within the range of 6,000 to 12,000 centistokes measured at 25° C. are usually suitable.

Suitable thickeners, include, among others, sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose, and starch amylose, locust bean gum, electrolytes such as sodium or ammonium chloride, saccharides such as fructose and glucose, and derivatives of saccharides such as PEG-120 methyl glucose dioleate.

The perfumes which can be used in the compositions are the cosmetically acceptable perfumes. Colorants are used to confer a color to the composition and may generally be used. Although not required, it is preferred to employ an acid to adjust the pH within the range of 5 to 9 or more preferably within the range of 6 to 8 in the compositions of this invention. Any water soluble acid such as a carboxylic acid or a mineral acid is suitable. For example, suitable acids include mineral acids such as hydrochloric, sulfuric, and phosphoric, monocarboxylic acids such as acetic acid, lactic acid, or propionic acid; and polycarboxylic acids such as succinic acid, adipic acid and citric acid.

If for special purposes additional conditioners are desired, they may be added. For example, any of the well-known organic cationic hair conditioning components may be added. Some cationic conditioning components that may be used in the present invention to provide hair grooming include quaternary nitrogen derivatives of cellulose ethers, homopolymers of dimethyldiallyl-ammonium chloride: copolymers of acrylamide and dimethyldiallylammonium chloride, homopolymers or copolymers derived from acrylic acid or methacrylic acid containing cationic nitrogen functional groups attached to the polymer via ester or amide linkages, polycondensation products of N,N'-bis-(2,3-epoxypropyl)-piperazine or of piperazine-bis-acrylamide and piperazine, poly-(dimethylbutenylammonium chloride)-α,ω-bis-(triethanol-ammonium) chloride, and copolymers of vinylpyrrolidone and acrylic acid esters with quaternary nitrogen functionality. The above cationic organic polymers and others are described in more detail in U.S. Pat. No. 4,240,450 which is hereby incorporated by reference to further describe the cationic organic polymers. Other categories of conditioners such as monomeric quaternary amine salts may also be employed.

A preservative may be required and representative preservatives which may be employed include about 0.1–0.2 weight percent of compounds such as formaldehyde, dimethyloldimethylhydantoin, 5-bromo-5-nitro-1,3-dioxane, methyl- and propyl para-hydroxybenzoates, and mixtures of such benzoates with sodium dehydroacetate, sorbic acid, and imidazolidinyl urea.

The compositions of the present invention may also be formulated to include dyes, colorants, reducing agents, neutralizing agents, and preservatives, necessary for their application as permanent wave systems or hair dyes, for example. The active formulation can be applied in several different forms including lotions, gels, mousses, aerosols, and pump sprays, for example, and as conditioners and shampoos. The active ingredient may include a carrier, and suitable carrier fluids for hair care formulations are water as well as, for example, such fluids as alcohols namely ethanol or isopropanol, hydrocarbons and halogenated hydrocarbons as mineral spirits and trichloroethane, cyclic siloxanes, and aerosol propellants.

When the composition is intended for aerosol application, propellant gases can be included such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

The concept of the present invention is illustrated in the following examples and tables in which a conditioning shampoo composition is set forth containing 10–80 percent by weight of a volatile carrier such as water; 0.5–5.0 percent by weight of the silicone mixture of a trisiloxane polyether and an amine functional siloxane polymer; 7–35 percent by weight of at least one surfactant; 1–7 percent by weight of a foam booster; less than about two percent by weight of a thickener; and a pH adjusting agent in an amount sufficient to establish a composition pH of between about 5–7. Preferably, the amount of the silicone mixture present in the composition constitutes 5–50 percent by weight of the amine functional siloxane polymer based on the total weight of the silicone mixture present in the composition.

EXAMPLE I

Seven shampoo base compositions were prepared containing the various ingredients shown in grams in Table I below. Phases A and B were each prepared separately by mixing together the ingredients in each phase until uniform. Phases A and B were combined, mixed together until uniform, and the pH of the resulting shampoo base composition was adjusted to a pH of 5–7 with citric acid.

In Table I, "Silicone 1" is used to indicate an amine functional silicone polymer according to the invention having the formula:

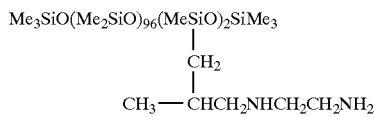

in which Me represents the methyl radical. "Silicone 2" in Table I represents a trisiloxane polyether in accordance with the present invention.

The particular trisiloxane polyether "Silicone 2" used in this example was a compound conforming to the first generic formula set forth previously for the trisiloxane polyethers, in which $R^a$ was a methyl radical; $R^b$ was a $-CH_2CH_2CH_2O-$ radical; $R^c$ was hydrogen; the integer p had a value of twelve; and the integer s had a value of zero.

TABLE I

| Ingredients | SHAMPOO BASE FORMULAS (%) | | | | | | |
|---|---|---|---|---|---|---|---|
| | 1 | 2 | 3 | 4 | 5 | 6 | 7 |
| PHASE A: | | | | | | | |
| Ammonium Lauryl Sulfate (30%) | 4.6 | 4.6 | 30.0 | 30.0 | 4.6 | 30.0 | 30.0 |
| Water | 10.0 | 10.0 | 64.6 | 64.6 | 10.0 | 65.0 | 65.0 |
| Ammonium Chloride | .05 | .05 | 1.5 | 1.5 | .05 | 1.0 | 1.0 |
| PHASE B: | | | | | | | |
| Cocamide DEA | .47 | .47 | 3.0 | 3.0 | .47 | 3.0 | 3.0 |
| Silicone 1 | — | — | 1.0 | 1.0 | — | 0.5 | 0.5 |
| Silicone 2 | — | 0.15 | — | 1.1 | — | — | 1.0 |
| ADDED TO A & B | | | | | | | |
| Citric Acid | 0.5 | 0.5 | 0.5 | 0.5 | 0.5 | 0.5 | 0.5 |

In Table I, ammonium lauryl sulfate was employed as anionic surfactant. Ammonium chloride was used as the thickening agent. The foam booster was a nonionic surfactant Cocamide DEA which is the CTFA adopted name for coconut fatty acid diethanolamide. The volatile carrier was water, and as noted above, citric acid was used as the pH adjusting agent.

EXAMPLE II

Shampoo base compositions 1–7 shown in Table I were tested on hair for conditioning benefits. Shampoo base composition 4 and 7 contained the silicone mixture as indicated in Table I and are representative of the present invention. Shampoo base composition 1 and 5 contained no silicone as shown in Table I, and were used as the blank control shampoos.

Hair tresses were shampooed with a commercial grade shampoo and dried. Each tress was wetted and 0.5 grams of the test shampoo was applied to the tress. The test shampoo was worked into the tress for thirty seconds. The tress was rinsed for thirty seconds with water and detangled by passing the wide part of a comb through the tress one time. The tress was hung to dry and evaluated after the elapse of twenty-four hours. The tress was evaluated for wet and dry combing, and dry feel. Subjective combing evaluations were conducted by volunteers who assigned values to each tress between one and 5, with one being the best and five the worst. The results for shampoo base compositions 1–7 are shown in Table II.

TABLE II

| Shampoo Base | Wet Combing | Dry Combing | Dry Feel | PWC |
|---|---|---|---|---|
| 1 | 3 | 2 | 2 | — |
| 2 | 4 | 2.5 | 2 | — |
| 3 | 1.5 | 1.5 | 2 | — |
| 4 | 1.0 | 1.25 | 2 | — |
| 5 | 3.5 | 2 | 2 | 4 |
| 6 | 2.5 | 2.5 | 1.75 | 3 |
| 7 | 1.75 | 1.25 | 2 | 1.5 |

PWC in Table II indicates for Shampoo Bases Nos. 5–7 an additional evaluation for "Prolonged Wet Combing". The results for "Prolonged Wet Combing" (PWC) obtained with the Shampoo Base No. 7 which is representative of the present invention in comparison with Shampoo Bases Nos. 5 and 6, reveals the dramatic improvement in conditioning which can be obtained by formulating conditioning shampoos according to the concepts disclosed herein. This is even more revealing when it is considered that Shampoo Base No. 7 contained less of the amine functional siloxane polymer than was present in Shampoo Base No. 4.

Regarding Shampoo Bases Nos. 1–4, the results of Table II reveal a synergy obtained in conditioning with compositions formulated according to the precepts of the invention. Thus, conditioning was better for Shampoo Base No. 4 which contained both the amine functional siloxane polymer and the trisiloxane polyether, than was obtained with either of Shampoo Bases Nos. 2 or 3 which contained only the trisiloxane polyether and the amine functional siloxane polymer, respectively.

It will be apparent from the foregoing that many other variations and modifications may be made in the compounds, compositions, and methods described herein without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. A composition comprising a mixture of an amine functional silicone and a trisiloxane polyether, the amine functional silicone having the formula:

wherein R' denotes an alkyl group of 1 to 4 carbons or a phenyl group with the proviso that at least 50 percent of the total number of R' groups are methyl; Q denotes an amine functional substituent of the formula—R"Z in which R" is a divalent alkylene radical of 3 to 6 carbon atoms and Z is a monovalent radical selected from the group consisting of $-NR_2'''$, and $-NR'''(CH_2)nNR_2'''$; wherein R''' denotes hydrogen or an alkyl group of 1 to 4 carbons; and n is a positive integer having a value of from 2 to 6; z has a value of 0 or 1; x has an average value of 25 to 10,000; y has an average value of 0 to 100 when z is 1, y has an average value of 1 to 100 when z is 0; with the proviso that in all cases y has an average value that is not greater than one tenth the average value of x; the trisiloxane polyether having the formula:

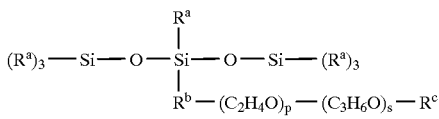

wherein $R^a$ is an alkyl group of one to six carbon atoms; $R^b$ is a linking group and a radical selected from the group consisting of —O—, —$C_mH_{2m}$—, —$C_mH_{2m}O$—, —$C_mH_{2m-2}$—, —$C_mH_{2m-2}O$— and —$C_mH_{2m}CO_2$—; $R^c$ is a terminating radical selected from the group consisting of hydrogen, an aryl group, an acyl group, and an alkyl group of one to six carbon atoms; m is an integer having a value two to eight; p and s are each integers having values such that the oxyalkylene segment —$(C_2H_4O)_p$—$(C_3H_6O)_s$— has a molecular weight in the range of 250 to 5,000; the oxyalkylene segment having fifty to one hundred mole percent of oxyethylene units —$(C_2H_4O)_p$— and zero to fifty mole percent of oxypropylene units —$(C_3H_6O)_s$—.

2. A composition according to claim 1 in which $R^a$ and the terminating radical $R^c$ are methyl groups; m is three or four; and the values of p and s are such as to provide a molecular weight of the oxyalkylene segment —$(C_2H_4O)_p$—$(C_3H_6O)_s$— of between 250 to 1000.

3. A composition according to claim 1 in which the linking group $R^b$ is the radical —$(CH_2)_3$—O—.

4. A composition according to claim 1 in which the amine functional silicone constitutes from five to fifty percent by weight of the mixture.

5. A composition according to claim 1 in which the mixture includes a polydiorganosiloxane gum having the average unit formula $R_aSiO_{4-a/2}$ in which each R substituent is a monovalent radical selected from the group consisting of a methyl radical, a vinyl radical, a phenyl radical, and a 3,3,3-trifluoropropyl radical, a has an average value of 1.95–2.005 inclusive, at least ninety percent of the total number of R substituents being methyl radicals, the molecules of the polydiorganosiloxane gum being terminated by a substituent selected from the group consisting of silanols, alkoxys, and $R_3SiO_{0.5}$, in which R is the same as defined above.

* * * * *